United States Patent [19]

Harita et al.

[11] 4,026,896
[45] May 31, 1977

[54] AROMATIC AMIDOCARBOXYLIC ACIDS AND PHARMACEUTICAL COMPOSITIONS THEREOF

[75] Inventors: Kozaburo Harita, Matsumoto; Yukiyoshi Ajisawa, Okaya; Kinji Iizuka, Nagoya; Michio Toda; Yukihiko Kinoshita, both of Matsumoto; Tetsuhide Kamijo, Shiojiri; Michihiro Kobayashi, Matsumoto, all of Japan

[73] Assignee: Kissei Yakuhin Kogyo Kabushiki Kaisha (Kissei Pharmaceutical Co. Ltd.), Nagano, Japan

[22] Filed: Apr. 16, 1975

[21] Appl. No.: 568,423

[30] Foreign Application Priority Data

Apr. 18, 1974 Japan .............................. 49-43675
Apr. 18, 1974 Japan .............................. 49-43676
Apr. 18, 1974 Japan .............................. 49-43678

[52] U.S. Cl. ..................... 424/282; 260/247.2 A; 260/293.58; 260/293.77; 260/340.5; 260/471 R; 260/479 R; 260/501.11; 260/518 R; 260/518 A; 260/519; 424/248.54; 424/267; 424/309; 424/311; 424/316; 424/319

[51] Int. Cl.² ..................................... C07C 103/84

[58] Field of Search ........... 260/518 R, 518 A, 519, 260/340.5, 501.11, 479 R; 424/319, 316, 282

[56] References Cited

UNITED STATES PATENTS

| | | | |
|---|---|---|---|
| 3,488,737 | 1/1970 | Gordon ..................... | 260/518 R X |
| 3,781,328 | 12/1973 | Witte et al. .................... | 260/519 X |
| 3,940,422 | 2/1976 | Harita et al. .................... | 260/340.5 |

*Primary Examiner*—Richard L. Raymond
*Attorney, Agent, or Firm*—William J. Daniel

[57] ABSTRACT

New aromatic amidocarboxylic acid derivatives of the general formula:

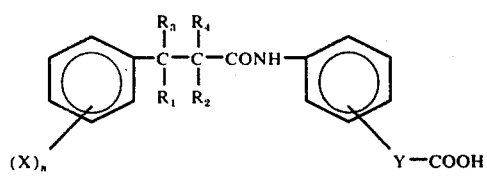

wherein $R_1$ and $R_2$ each represent a hydrogen atom or an alkyl group with 1–4 carbon atoms; $R_3$ and $R_4$ each represent a hydrogen atom or may be combined together to form an additional chemical bond; X represents a hydroxyl group, a halogen atom, a straight or branched chain saturated or unsaturated alkyl group with 1–4 carbon atoms, a straight or branched chain saturated or unsaturated alkoxy group with 1–4 carbon atoms, an acyloxy group with 1–4 carbon atoms, or a cycloalkyl group with up to 6 carbon atoms; $n$ is zero or an integer of 1–3 with the proviso that when $n$ is 2 or 3, X's may be the same or different and that when two X's are commonly the alkyl or alkoxy group, both X's may be combined together to form a ring; and Y represents a straight or branched chain alkylene group or a straight or branched chain oxyalkylene group connected to the benzene nucleus through an oxygen atom, as well as physiologically acceptable salts thereof.

The new compounds possess a strong antiallergic effect and are thus useful for the treatment of asthma, hay fever, urticaria and atopic dermatitis.

The above-mentioned aromatic amidocarboxylic acid and a salt thereof are prepared, for example, by reacting a reactive functional derivative of the general formula:

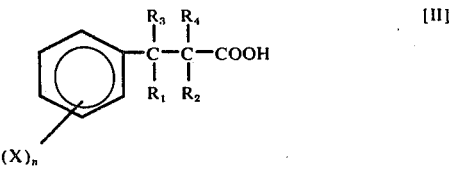

wherein $R_1$, $R_2$, $R_3$, $R_4$, X and $n$ have the same meanings as given above, with an aminophenylalkylcarboxylic acid derivative or an aminophenoxyalkylcarboxylic acid derivative of the general formula:

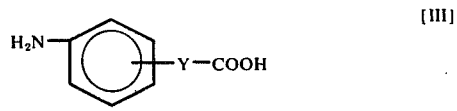

wherein Y has the same meaning as given above, and if desired, converting the resulting amidocarboxylic acid into a corresponding salt thereof or vice versa.

7 Claims, No Drawings

AROMATIC AMIDOCARBOXYLIC ACIDS AND PHARMACEUTICAL COMPOSITIONS THEREOF

BACKGROUND OF THE INVENTION

This invention relates to new aromatic amidocarboxylic acid derivatives. More particularly, this invention relates to cinnamoylaminophenylalkylcarboxylic acid derivatives and cinnamoylaminophenoxyalkylcarboxylic acid derivatives which exhibit a strong antiallergic effect when administered orally to mammalia including humans.

Hitherto, disodium chromoglycate was known as an antiallergic agent effective for inhibiting release of chemical mediators from cells caused by an antigen-antibody reaction. However, such pharmacological effect is not at all expected when this compound is administered orally, and the extent to which this compound is applicable is naturally limited. Thus, development of an antillergic agent which can exhibit a satisfactory therapeutic effect by oral administration has long been demanded in the field of medicine.

On the other hand, unsubstituted cinnamoylaminobenzoic acid which is an analogue of the end products of the present invention was already synthetized by Reinicke and publicly known (Liebig's Annalen der Chemie, vol. 341, pages 94–96). However, this compound shows only a slightly weak antiallergic effect when administered orally to mammalia, and so hardly applicable as practically effective medicine. As a result of our research carried out on antiallergic effects of various cinnamoylaminobenzoic acid derivatives, we found that certain kinds of nucleus-substituted cinnamoylaminobenzoic acid derivatives had a strong antiallergic effect. An invention based on the above finding was already applied for by us in Japan as Japanese Patent Appln. No. 7359/73. As a result of our further research carried out on antiallergic effects of cinnamoylaminophenylalkylcarboxylic acid derivatives and cinnamoylaminophenoxyalkylcarboxylic acid derivatives, it has now been found that a series of these amidocarboxylic acid derivatives possess an extremely strong antiallergic effect.

BRIEF SUMMARY OF THE INVENTION

Accordingly, it is a primary object of this invention to provide compounds which exhibit a strong antiallergic effect when administered orally to mammalia including humans.

It is another object of this invention to provide new amidocarboxylic acid derivatives possessing a certain pharamcalogical effect.

It is still another object of this invention to provide unsubstituted or substituted cinnamoylaminophenylalkylcarboxylic acids, unsubstituted or substituted cinnamoylaminophenoxyalkylcarboxylic acids, unsubstituted or substituted hydrocinnamoylaminophenylalkylcarboxylic acids and unsubstituted or substituted hydrocinnamoylaminophenoxyalkylcarboxylic acids as well as physiologically acceptable salts thereof.

It is a further object of this invention to provide a method of treating allergies by administering the above-mentioned compounds to patients suffering from same.

Other objects, features and merits of this invention will become more fully apparent from the following description.

DETAILED DESCRIPTION OF THE INVENTION

It has now been found, surprisingly, that compounds of the general formula:

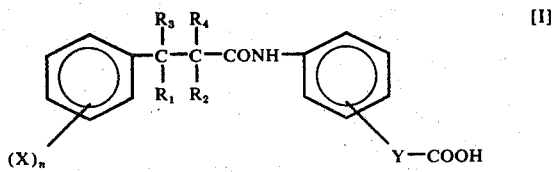

wherein $R_1$ and $R_2$ each represent a hydrogen atom or an alkyl group with 1–4 carbon atoms; $R_3$ and $R_4$ each represent a hydrogen atom or may be combined together to form an additional chemical bond; X represents a hydroxyl group, a halogen atom, a straight or branched chain saturated or unsaturated alkyl group with 1–4 carbon atoms, a straight or branched chain saturated or unsaturated alkoxy group with 1–4 carbon atoms, an acyloxy group with 1–4 carbon atoms, or a cycloalkyl group with up to 6 carbon atoms; $n$ is zero or an integer of 1–3 with the proviso that when $n$ is 2 or 3, X's may be the same or different and that when two X's are commonly the alkyl or alkoxy group, both X's may be combined together to form a ring; and Y represents a straight or branched chain alkylene group or a straight or branched chain oxyalkylene group connected to the benzene nucleus through an oxygen atom, can inhibit an experimental anaphylaxis (for example, inflammation of the skin caused by an antigen-antibody reaction between reagin and its peculiar antigen) by oral administration to patients. In view of these characteristic properties, it is expected that these compounds possess an antiallergic action and are effective for the therapeutic treatment of diseases caused by allergies such as asthma, hay fever, urticaria and atopic dermatitis.

In the compounds of this invention, the nuclear substituent X may not necessarily be present; the unsubstituted compounds also possess a strong antiallergic action. In case the compounds carry a nuclear substituent or substituents, however, their antiallergic action is further enhanced. Illustrative of preferable nuclear substituents are a hydroxyl group, an alkyl group, an alkoxy group, acetoxy group and a halogen atom. In case the nuclear substituent is an alkyl or alkoxy group or groups, they may be a straight or branched chain saturated or unsaturated one. As long as the number of carbon atoms in such groups is 1–4, no significant change was found in the strength of antiallergic action.

In case the nuclear substituents are two alkyl or alkoxy groups, they may be connected together to form a cyclic group. For example, methylenedioxycinnamoylaminophenylalkylcarboxylic acids also possess a strong antiallergic action. The halogen atoms as nuclear substituents may be chlorine atoms, fluorine atoms and bromine atoms. The compound having such nuclear halogen atoms are similarly strong in antiallergic action.

The most preferable nuclear substituent is the alkoxy group. The number of this nuclear substituent is limited to an extent of 1–3. In general, however, the antiallergic action becomes stronger as the number of nuclear substituents becomes larger.

In the aminophenylalkylcarboxylic acids and aminophenoxyalkylcarboxylic acids of this invention, the nuclear position of the alkylcarboxyl or oxyalkylcarboxyl group may be in any of the 2-, 3- and 4-positions. As the sort, position and number of the nuclear substituents (X) have a complicated and mutual influence on the antiallergic action, a preferable position of the substituents in the nucleus cannot be determined. The alkylene group has 1-6 carbon atoms and may be of a straight or branched chain.

Salts of these carboxylic acids, for example, alkali metal salts are as high in the antiallergic action as the corresponding free acid.

The compounds of the above general formula [I] can be prepared by reacting a reactive functional derivative of an aromatic carboxylic acid of the general formula:

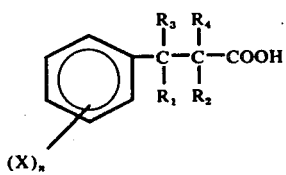

wherein $R_1$, $R_2$, $R_3$, $R_4$, X and n have the same meanings as given above, with an aminophenylalkylcarboxylic acid or an aminophenoxyalkylcarboxylic acid of the general formula:

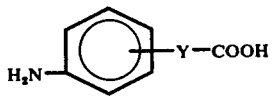

wherein Y has the same meaning as given above, or alternatively by reacting an aromatic carboxylic acid of the above general formula [II] or a reactive functional derivative thereof with an aminophenylalkylcarboxylic acid ester or an aminophenoxyalkylcarboxylic acid ester of the general formula:

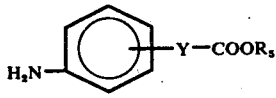

wherein Y has the same meaning as given above and $R_5$ represents an alkyl, haloalkyl, benzyl or tetrahydropyranyl group, to prepare an aromatic amidocarboxylic acid derivative of the general formula:

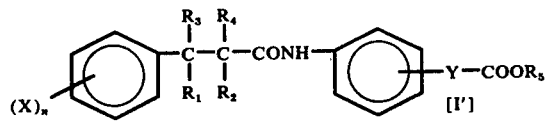

wherein $R_1$, $R_2$, $R_3$, $R_4$, $R_5$, X, Y and n have the same meanings as given above, and thereafter, hydrolizing this derivative to convert the ester group into the free carboxyl group.

The aromatic carboxylic acids of the above general formula [II] are known compounds and can easily be prepared according to methods disclosed in literature. The aromatic carboxylic acids having an unsaturated bond involve two isomers, i.e., cis-form and trans-form, whichever may be employed for this invention. Illustrative of the aromatic carboxylic acids of the general formula [II] are aromatic saturated carboxylic acids such as hydrocinnamic acid, 2-, 3- or 4-methylhydrocinnamic acid, 2-, 3- or 4-ethylhydrocinnamic acid, 2-, 3- or 4-propylhydrocinnamic acid, 2-, 3- or 4-hydroxyhydrocinnamic acid, 2-, 3- or 4-methoxyhydrocinnamic acid, 2-, 3- or 4-ethoxyhydrocinnamic acid, 2-, 3- or 4-chlorohydrocinnamic acid, 2-, 3- or 4-bromohydrocinnamic acid, 2-, 3- or 4-fluorohydrocinnamic acid, 2, 4-, 2,5- or 3,4-dimethylhydrocinnamic acid, 2,4-diethylhydrocinnamic acid, 2,3-, 2,4-, 2,5-, 2,6-, 3,4- or 3,5-dihydroxyhydrocimmamic acid, 2,3-, 2,4-, 2,5-, 2,6-, 3,4- or 3,5-dimethoxyhydrocinnamic acid, 2,3-, 2,4-, 2,5-, 2,6-, 3,4- or 3,5-diethoxyhydrocinnamic acid, 2,3-, 2,4- or 3,4-dipropoxyhydrocinnamic acid, 2-hydroxy-3-methoxyhydrocinnamic acid, 3-hydroxy-4-methoxyhydrocinnamic acid, 3-ethoxy-4-methoxyhydrocinnamic acid, 4-hydroxy-3-methoxyhydrocinnamic acid, 2-ethoxy-3-methoxyhydrocinnamic acid, 3-ethoxy-4-methoxyhydrocinnamic acid, 4-ethoxy-3-methoxyhydrocinnamic acid, 3-methoxy-2-propoxyhydrocinnamic acid, 3-methoxy-4-propoxyhydrocinnamic acid, 3,4-methylenedioxyhydrocinnamic acid, 2,4-, 2,6- or 3,4-dichlorohydrocinnamic acid, 2,3,4-, 2,4,5- or 3,4,5-trimethoxyhydrocinnamic acid, 2-bromo-4-hydroxy-5-methoxyhydrocinnamic acid, 4-isopropylhydrocinnamic acid, 3- or 4-isopropoxyhydrocinnamic acid, 3- or 4-isobutoxyhydrocinnamic acid, 3- or 4-sec-butoxyhydrocinnamic acid, 3-methoxy-4-isopropoxyhydrocinnamic acid, 2-, 3- or 4-allyloxyhydrocinnamic acid, 2-, 3- or 4-methallyloxyhydrocinnamic acid, 3-methoxy-4-allyloxyhydrocinnamic acid, 3-methoxy-4-methallyloxyhydrocinnamic acid, 2-, 3- or 4-acetoxyhydrocinnamic acid, 3,4-trimethylenehydrocinnamic acid, and α- and/or β-alkyl-substituted hydrocinnamic acids carrying substituents the same as those mentioned in the case of the above-mentioned hydrocinnamic acids; and aromatic unsaturated carboxylic acids such as cinnamic acid, 2-, 3- or 4-methylcinnamic acid, 2-, 3- or 4-ethylcinnamic acid, 2-, 3- or 4-propylcinnamic acid, 2-, 3- or 4-hydroxycinnamic acid, 2-, 3- or 4-methoxycinnamic acid, 2-, 3- or 4-ethoxycinnamic acid, 2-, 3- or 4-propoxycinnamic acid, 2-, 3- or 4-butoxycinnamic acid, 2-, 3- or 4-fluorocinnamic acid, 2-, 3- or 4-chlorocinnamic acid, 2-, 3- or 4-bromocinnamic acid, 2,4- or 2,5 or 3,4-dimethylcinnamic acid, 2,4-diethylcinnamic acid, 2,3-, 2,4-, 2,5- 2,6-, 3,4- or 3,5-dihydroxycinnamic acid, 2,3-, 2,4-, 2,5-, 2,6-, 3,4- or 3,5-dimethoxycinnamic acid, 2,3-, 2,4-, 2,5-, 2,6-, 3,4- or 3,5-diethoxycinnamic acid, 2,3-, 2,4- or 3,4-dipropoxycinnamic acid, 2-hydroxy-3-methoxycinnamic acid, 3-hydroxy-4-methoxycinnamic acid, 4-hydroxy-3-methoxycinnamic acid, 2-ethoxy-3-methoxycinnamic acid, 3-ethoxy-4-methoxycinnamic acid, 4-ethoxy-3-methoxycinnamic acid, 3-methoxy-2-propoxycinnamic acid, 3-methoxy-4-propoxycinnamic acid, 3,4-methylenedioxycinnamic acid, 2,4-, 2,6- or 3,4-dichlorocinnamic acid, 2,3,4-, 2,4,5- or 3,4,5-trimethoxycinnamic acid, 2-bromo-4-hydroxy-5-methoxycinnamic acid, 4-isopropylcinnamic acid, 3- or 4-isopropoxycinnamic acid, 3- or 4-isobutoxycinnamic acid, 3- or 4-sec-butoxycinnamic acid, 3-methoxy-4-isoproxycinnamic acid, 2-, 3- or 4-allyloxycinnamic acid, 2-, 3- or 4-methallyloxycinnamic acid, 3-methoxy-4-allyloxycinnamic acid, 3-methoxy-4-methallyloxycinnamic acid, 2-, 3- or 4-acetoxycinnamic acid, 3,4-trimethylenecinnamic acid, and α- and/or β-alkylsubstituted cinnamic acids carrying substituents the same as those mentioned in the case of the above-mentioned cinnamic acids.

The aminophenylalkylcarboxylic acids or aminophenoxyalkylcarboxylic acids of the above general formula [III] are known compounds and can be prepared according to methods referred to in literature. Examples of such aminophenylalkylcarboxylic acids and aminophenoxyalkylcarboxylic acids include 2-, 3- or 4-aminophenylacetic acid, α-(2-, 3- or 4-aminophenyl)propionic acid, β-(2-, 3- or 4-aminophenyl)-propionic acid, α-(4-aminophenyl)propionic acid, α-, β- or γ-(4-aminophenyl)-n-butyric acid, ω-(4-aminophenyl)-n-valeric acid, ω-(4-aminophenyl)-n-capronic acid, 2-, 3- or 4-aminophenoxyacetic acid, α-(4-aminophenoxy)-propionic acid, α-(4-aminophenoxy)-isobutyric acid and α-(4-aminophenoxy)-n-butyric acid. Examples of the aminophenylalkylcarboxylic acid esters and aminophenoxyalkylcarboxylic acid esters of the above general formula [III'] include alkyl esters, haloalkyl esters, benzyl esters, tetrahydropyranyl esters of the above-mentioned carboxylic acids.

The aromatic amidocarboxylic acid derivatives of this invention can be obtained by reacting an aromatic carboxylic acid of the general formula [II] in the presence or absence of an inert solvent with an aromatic aminocarboxylic acid of the general formula [III] or an ester of the general formula [III'] by the aid of an appropriate condensing agent. Suitable inert solvents in this case include dioxane, chloroform, methylene chloride, acetone, methyl ethyl ketone, benzene, toluene and tetrahydrofuran. Utilizable as the condensing agent are polyphosphoric acid, polyphosphoric acid esters, phosphorus pentoxide, phosphorus oxychloride and phosphorus halides.

The process for producing the end products is carried out preferably by dissolving a compound of the general formula [II] in a mixture of dioxane in an amount of 5–100 times as much as the amount of the compound of the general formula [II] and pyridine in an amount of 0–20 molar proportion, adding to the mixture phosphorus oxychloride in an amount of 5–100 molar proportion and a compound of the general formula [III] or [III'] in an amount of 1–2 molar proportions, and heating the whole for several hours. The reaction product is concentrated under reduced pressure. If necessary, an aqueous solution of sodium hydroxide is added to the concentrated reaction product and the mixture is warmed to effect hydrolysis. The concentrated reaction product is, directly or after being subjected to the hydrolysis, poured into water and hydrochloric acid is then added to the aqueous mixture to make it weakly acidic. The precipitated crystals are collected by filtration and then recrystallized from a suitable organic solvent to obtain the end product. In case a compound of the general formula [II] is an aromatic carboxylic acid carrying a hydroxy group or groups on the benzene nucleus, such compound is preferably protected in the hydroxy group(s) with acetyl group or the like prior to the reaction with a compound of the general formula [III] or [III']. Such protective group can be split off by a usual manner.

The aromatic amide derivatives of this invention can also be obtained by reacting a reactive functional derivative of a compound of the general formula [II] with a compound of the general formula [III].

Examples of such reactive functional derivative of a compound of the general formula [II] include acid halides, acid anhydrides, mixed acid anhydrides, esters and the like carboxylic acid derivatives. Such reactive functional derivatives can easily be derived from aromatic carboxylic acids of the general formula [II] according to a usual manner. For example, acid chlorides can easily be obtained by refluxing for several hours the aromatic carboxylic acid and thionyl chloride in the presence of benzene or in the absence of any solvent. Mixed acid anhydrides can be obtained, for example, by reacting the aromatic carboxylic acid with a chloroformic acid ester or a sulfonic acid halide. Such reactive functional derivative may once be isolated from the reaction system or may continuously be used, without isolation, for the reaction with an aminophenylalkylcarboxylic acid or aminophenoxyalkylcarboxylic acid of the general formula [III] or with an ester thereof represented by the general formula [III'].

For example, when an acid halide is employed as the reactive functional derivative, the reactants are reacted together in an inert solvent in the presence of a basic substance. Illustrative of the basic substance in this case are organic tertiary bases such as triethylamine, pyridine, 2-, 3- or 4-methylpyridine and N,N-dimethylaniline and inorganic bases such as sodium carbonate, sodium bicarbonate and potassium bicarbonate. Preferable examples of the inert solvent in this case include chloroform, methylene chloride, acetone, benzene, toluene, tetrahydrofuran, dioxane, dimethylformamide, water and a mixture of these solvents. Instead of using such basic substance, the reaction may be carried out by using a compound of the general formula [III] in an excess amount, e.g. more than 2 molar proportions to the compound of the general formula [II]. This process is carried out preferably by dissolving a compound of the general formula [III] in a mixture of chloroform in an amount of 5–20 times as much as the amount of the reactive functional derivative of a compound of the general formula [II] and pyridine in an amount of 2–100 molar proportions to the reactive functional derivative, adding dropwise a solution of the reactive functional derivative in chloroform to the mixture under cooling and agitation and then heating the whole for several hours to effect reaction. The reaction product is concentrated under subatmospheric pressure and the residual liquid is poured into water. Hydrochloric acid is then added to the aqueous mixture to make it weakly acidic. The precipitated crystals are collected by filtration and then recrystallized from a suitable solvent to obtain the end product.

In case an ester of the general formula [III'] is used, a protective group for the carboxyl group can be split off according to a usual method after the condensation reaction, if necessary.

The compounds of the above general formula [I] can also be prepared by condensing a malonanilic acid derivative of the general formula:

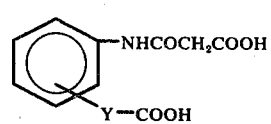

[IV]

wherein Y has the same meaning as given above, with an aromatic aldehyde of the general formula:

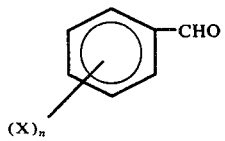
[V]

wherein X and n have the same meanings as given above.

In this case, compounds of the general formula [IV] are new and can easily be prepared by reacting an aminophenylalkylcarboxylic acid or an aminophenoxyalkylcarboxylic acid of the general formula [III] with a reactive functional derivative of malonic acid, for example, malonic hemichloride. The aromatic aldehydes of the general formula [V] may be nucleus-substituted in a similar manner to the case of the aromatic carboxylic acids of the general formula [II]. These aldehydes are known compounds and can be prepared according to methods disclosed in literature.

The above condensation reaction can be carried out in a manner known per se; an aldehyde of the general formula [V] is reacted in the presence or absence of an inert solvent with a malonanilic acid derivative of the general formula [IV] in the presence of a basic substance. Examples of the basic substance in this case include organic primary amines such as ammonia, methylamine, ethylamine, butylamine, amylamine, aniline and ethanolamine; organic secondary amines such as diethylamine, dibutylamine, piperidine and morpholine; organic tertiary amines such as pyridine, quinoline, lutidine, N,N-dimethylaniline, diethylaminoethanolamine and triethanolamine; inorganic bases such as sodium carbonate, potassium carbonate and potassium acetate; and salts of these organic bases such as hydrochlorides, acetates and malonates. Besides these, ion exchange resins such as Amberlite 1R-4B, Dowex 3B and the like as well as acetates, benzoates, etc. can also be employed. The basic substance may be used alone or in a mixture of at least two. Examples of the inert solvent utilizable in this case include methanol, ethanol, isopropanol, butanol, chloroform, dichloromethane, dioxane, ethyl ether, isopropyl ether, dimethylformamide, dimethylsulfoxide and acetic acid. An organic base such as pyridine may be used as a solvent for the reaction.

This process is carried out preferably by dissolving a compound of the general formula [IV] and a compound of the general formula [V] in a mixture of dry pyridine in an amount of 10–20 times as much as the amount of these compounds and a catalytic amount of piperidine, heating the mixture for several hours in an oil bath maintained at 80°–100° C, distilling the solvent under reduced pressure, dissolving the residual product in a small amount of an alcohol, adding an appropriate amount of ice water to the alcoholic solution and making it acidic with hydrochloric acid. The precipitated crystals are collected by filtration and then recrystallized from a suitable solvent thereby yielding the end product.

For preparing the end product of the general formula [I] wherein Y represents a straight or branched chain oxyalkylene group, an aromatic carboxylic acid of the general formula [II] or a reactive functional derivative thereof is first reacted with an aminophenol of the general formula:

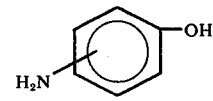
[VI]

and the resulting amidophenol of the general formula:

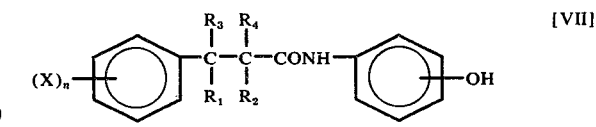
[VII]

wherein X, n, $R_1$, $R_2$, $R_3$ and $R_4$ have the same meanings as given above, is then reacted with an aliphatic carboxylic acid or an ester thereof represented by the general formula:

$$Z - \text{alkylene} - COOR_6 \quad [VIII]$$

wherein Z is an acid residue, alkylene is a straight or branched chain alkylene group and $R_6$ is a hydrogen atom or a carboxyl group-protecting group selected from hydrocarbyl groups, substituted hydrocarbyl groups and cyclic ether groups, to form a compound of the general formula:

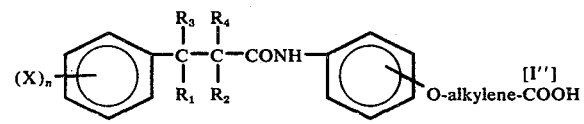
[I″]

wherein X, n, $R_1$, $R_2$, $R_3$ and $R_4$ have the same meanings as given above, which is the desired end product.

The amidophenol derivative of the general formula [VII] can be prepared, for example, by stirring an acid chloride of an aromatic carboxylic acid of the general formula [II] and an aminophenol of the general formula [VI] for 2–3 hours at room temperature in an inert solvent such as chloroform in the presence of a basic material such as pyridine, heating the mixture for a given period of time, concentrating the reaction mixture under reduced pressure, pouring the residue into water, making the aqueous solution acidic with hydrochloric acid, collecting the precipitated crystals by filtration and thereafter, recrystallizing the crystals from a suitable solvent.

The O-alkylation reaction for a compound of the general formula [VII] can be carried out according to a conventional method. For example, anhydrous potassium carbonate in 1–5 molar proportions to the compound of the general formula [VII] is suspended in methyl ethyl ketone in an amount of 10–50 times as much as the amount of the compound of the general formula [VII]. To this suspension are added a compound of the general formula [VII] and a compound of the general formula [VIII]. The mixture is then heated under reflux for 3–72 hours to effect reaction. The reaction mixture is filtered and the filtrate is concentrated. The residue is treated with an acid and a base and, if necessary, the ester group is split off according to a conventional method. The residue thus treated is then acidified with hydrochloric acid and the precipitated crystals are collected by filtration and recrystallized from a suitable organic solvent to prepare the end product.

For preparing the end product of this invention represented by the general formula [I] wherein $R_3$ and $R_4$ each stand for a hydrogen atom and X for a substituent free of an unsaturated bond, a cinnamoylamide derivative of the general formula:

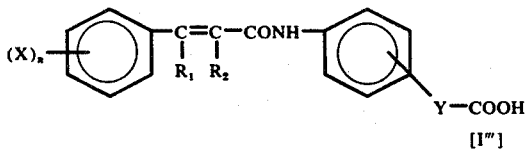

wherein $R_1$, $R_2$, X, Y and $n$ have the same meanings as given above, is prepared from the corresponding starting materials according to a method similar to that described above, and thereafter, reduced by hydrogenation.

The resulting compound of the general formula [I] having a carboxyl group can be converted in a conventional manner into a salt thereof. For example, a compound of the general formula [I] can easily be converted into a sodium salt thereof by adding an aqueous solution of an equivalent amount of sodium hydroxide to an alcoholic solution of the compound. In a similar manner, a compound of the general formula [I] can be converted into its inorganic salt such as potassium salt, magnesium salt or aluminum salt or organic salt such as morpholinium salt, piperadinium salt or triethanolammonium salt. The aromatic amide derivatives of this invention possess a special effect to the action caused by an antigen-antibody reaction and thus are widely applicable as a therapeutic medicine for diseases caused by allergies.

This invention will now be explained in more detail by way of examples which are given merely for the purpose of illustration and are not to be construed as limiting the scope of the invention. In each example, the melting point is not corrected.

EXAMPLE 1

To 2 ml of pyridine and 2 drops (about 0.03 ml) of piperidine were added 150 mg of 3,4-methylenedioxybenzaldehyde and 267 mg of 4-carboxymethoxymethylmalonanilic acid. The mixture was heated for 2-3 hours in an oil bath maintained at 80°–100° C. After completion of the reaction, the solvent was distilled off under reduced pressure and the residue was acidified with diluted hydrochloric acid whereupon crystals were precipitated. The crystals were collected by filtration, washed with water and then recrystallized from an aqueous alcohol whereby 229 mg of the desired 4-(3',4'-methylenedioxy-α-methylcinnamoylamino) phenoxyacetic acid were obtained. Yield: 71%, M.P. 167°–170° C. Below are the characteristics of this product.

IR-absorption spectra (KBr) $\nu$CO 1740cm$^{-1}$, 1650cm$^{-1}$;

NMR spectra (d$_6$-DMSO, 90MH$_z$) $\delta$ value: 2.09 (d, J = 1.0H$_z$, 3H, methyl hydrogen); 4.62 (s, 2H, methylene hydrogen); 6.04 (s, 2H, methylenedioxymethylene hydrogen); 6.8–7.7 (m, 8H, aromatic ring and olefinic hydrogen); 9.76 (s, 1H, carboxyl hydrogen);

Elementary analysis as $C_{19}H_{17}O_6N$ Calcd. C: 64.22; H: 4.82; N: 3.94; Found C: 64.03; H: 4.96; N: 3.81.

EXAMPLE 2

In 50 ml of methyl ethyl ketone were dissolved 1.3 g of 4-(4'-methylcinnamoylamino)-phenol, 0.8 g of sodium iodide and 0.9 g of ethyl α-bromopropionate. To this mixture was added 0.8 g of anhydrous potassium carbonate and the whole was heated under reflux and agitation for 20 hours. The reaction liquid was cooled and filtered and the filtrate was concentrated. The residue was then hydrolyzed by warming same in a mixture of 10 ml of a 10% aqueous solution of potassium hydroxide and 10 ml of ethanol.

The reaction liquid was poured into ice-hydrochloric acid whereupon crystals were precipitated out. The crystals were collected by filtration and recrystallized from an aqueous alcohol whereby 0.3 g of α-[4-(4'-methylcinnamoylamino)phenoxy]propionic acid was obtained. M.P. 200°–204° C. Below are the characteristics of this product.

IR-absorption spectra (KBr) $\nu$CO 1725 cm$^{-1}$, 1655 cm$^{-1}$;

Elementary analysis as $C_{19}H_{19}O_4N$ Calcd. C:70.14; H: 5,89; N: 4.31; Found C: 70.28; H: 5.96; N: 4.14.

NMR-spectra (d$_6$ - DMSO, 90 MH$_z$); $\delta$ value 1.35 (d, 3H, methyl hydrogen); 2.33 (s, 3H, methyl hydrogen as aromatic ring substituent); 3.15 (q, 1H, methyn hydrogen); 6.17–7.78 (m, 10H, olefinic, aromatic ring hydrogen); 10.7 (s, 1H carboxyl hydrogen).

EXAMPLE 3

1.8 Grams of 3-aminophenylacetic acid were dissolved in 20 ml of pyridine and 30 ml of dioxane. To the mixture was added dropwise under cooling and agitation a chloroform solution of 2.1 g of α-methyl-4-chlorocinnamoyl chloride. The mixture was heated under reflux for 2 hours and then concentrated under reduced pressure. The residue was poured into water and weakly acidified with hydrochloric acid. The precipitated crystals were collected by filtration and recrystallized from alcohol-water whereby 1.3 g of 3-(α-methyl-4'-chlorocinnamoylamino)phenylacetic acid were obtained. M.P. 154.5°–156° C. Below are the characteristics of this product.

Elementary analysis as $C_{18}H_{16}O_3NCl$ Calcd. C, 65.55; H, 4.89; O, 4.25; Found C, 65.83; H, 4.84; O, 4.11.

IR-absorption spectra (KBr) $\nu$CO 1700 cm$^{-1}$, 1650 cm$^{-1}$;

NMR spectra (d$_6$-DMSO, 90 MH$_z$) $\delta$ value 2.09 (d, 3H, J. 1.5 H$_z$ methyl hydrogen); 3.56 (s, 2H, methylene hydrogen);

6.89–7.72 (m, 9H, olefinic, aromatic ring hydrogen); 9.9 (s, 1H, carboxyl hydrogen).

330 Milligrams of 3-(α-methyl-4'-chlorocinnamoylamino)phenylacetic acid were dissolved in an alcohol and an equivalent amount of sodium hydroxide was added to the solution. The solution was warmed for 30 minutes and then concentrated under reduced pressure. Ether was added to the residual liquid to precipitate crystals which were then collected by filtration to obtain sodium 3-(α-methyl-4'-chlorocinnamoylamino)phenylacetate.

EXAMPLE 4

In a mixture of 10 ml of pyridine and 30 ml of chloroform were dissolved 1.8 g of 2-aminophenylacetic acid. To the mixture was added dropwise under cooling a solution of 1.9 g of 4-methylhydrocinnamoylchloride in chloroform. The mixture was refluxed for 2 hours and the reaction mixture was then concentrated under reduced pressure. The residual liquid was poured into water and the aqueous solution was weakly acidified with hydrochloric acid. The precipitated crystals were collected by filtration and recrystallized from alcohol-water whereby 1.4 g of (2-(4'-methylhydrocinnamoylamino)phenylacetic acid were obtained. M.P. 170°–172° C. Other characteristics of this compound were as follows:

Elementary analysis as $C_{18}H_{19}O_3N$ Calcd. C, 72.70; H, 6.44; N, 4,71; Found C, 72.54; H, 6.39; N, 4.48.

IR-absorption spectra (KBr) $\nu$CO 1695 cm$^{-1}$, 1650 cm$^{-1}$;

NMR spectra (d$_4$-DMSO, 90 MH$_z$) $\delta$ value 2.27 (s, 3H, methyl hydrogen); 2.50–3.0 m, 4H, methylene hydrogen between aromatic rings); 3.53 (s, 2H, methylene hydrogen); 7.0–7.45 (m, 8H, aromatic ring hydrogen; 9.3 (s, 1H, carboxyl hydrogen).

297 Milligrams of 2-(4'-methylhydrocinnamoylamino)phenylacetic acid were dissolved in an alcohol and an equivalent amount of sodium hydroxide was added to the solution. The solution was warmed for 30 minutes and then concentrated under reduced pressure. Ether was added to the residual liquid to precipitate crystals which were then collected by filtration to obtain sodium 2-(4'-methylhydrocinnamoylamino)-phenylacetate.

EXAMPLE 5

In a mixture of 50 ml of dioxane and 0.9 ml of pyridine were dissolved 1.03 g of 4-acetoxycinnamic acid and 1.07 g of ethyl 4-aminophenoxyacetate. To this mixture was added 0.85 g of phosphorus oxychloride. The mixture was then heated under reflux for 3 hours. The reaction mixture was concentrated under reduced pressure and 50 ml of a 10% aqueous solution of sodium hydroxide were added to the residue. The mixture was warmed for one hour in a water bath and weakly acidified with hydrochloric acid whereupon crystals were precipitated out. The crystals were collected by filtration and recrystallized from ethanol-water whereby 0.65 g of 4-(4'-hydroxycinnamoylamino)-phenoxyacetic acid was obtained. M.P. 267°–269° C. Other characteristics of this compound were as follows:

Elementary analysis as $C_{17}H_{15}O_5N$ Calcd. C, 65.17; H, 4.82; N, 4.47; Found C, 65.04; H, 4.76; N, 4.30.

IR-absorption spectra (KBr) $\nu$CO 1735 cm$^{-1}$, 1660 cm$^{-1}$;

NMR spectra (d$_6$-DMSO, 90 MHz); $\delta$ value 4.63 (s, 2H, methylene hydrogen); 6.45–7.72 (m, 10H, olefinic hydrogen, aromatic ring hydrogen); 9.90 (s, 1H, carboxyl hydrogen).

156 Milligrams of 4-(4'-hydroxycinnamoylamino)-phenoxyacetic acid were dissolved in an alcohol and an equivalent amount of sodium hydroxide was added to the solution. The solution was warmed for 30 minutes. After cooling, ether was added to the solution and the precipitated crystals were collected by filtration to obtain sodium 4-(4'-hydroxycinnamoylamino)phenoxyacetate.

EXAMPLE 6

In a mixture of 80 ml of water and 100 ml of dioxane were dissolved 1.4 g of sodium 2-aminophenylpropionate. To this mixture were added dropwise under ice cooling and agitation a solution of 0.98 g of 3-methoxycinnamoyl chloride in dioxan and 20 ml of a 1% aqueous solution of sodium hydroxide at the same time. After addition of these solutions, the mixture was stirred for 2 hours at room temperature and thereafter, the reaction mixture was concentrated under reduced pressure. Water was added to the residual liquid and the mixture was then made weakly acidic by the addition of hydrochloric acid. The precipitated crystals were collected by filtration and recrystallized from ethanol-water whereby 1.0 g of 2-(3'-methoxycinnamoylamino)phenylpropionic acid was obtained. M.P. 173°–174° C. Other characteristics of this compound were as follows:

Elementary analysis as $C_{19}H_{19}O_4N$ Calcd. C, 70.14; H, 5.89; N, 4.31; Found C, 70.05; H, 5.87; N, 4.01.

IR-absorption spectra (KBr) $\nu$CO 1705 cm$^{-1}$, 1660 cm$^{-1}$;

NMR spectra (d$_6$ acetone, 90 MHz); $\delta$ value 2.55–3.1 (m, 4H, methylene hydrogen); 3.81 (s, 3H, methoxy hydrogen); 6.75–7.9 (m, 10H, olefinic hydrogen, aromatic ring hydrogen); 9.03 (s, 1H, carboxyl hydrogen).

162 Milligrams of 2-(3'-methoxycinnamoylamino)-phenylpropionic acid were dissolved in an alcohol and an equivalent amount of sodium hydroxide was added to the solution. The mixture was warmed for 30 minutes and then concentrated under reduced pressure. The residue was taken up in a small amount of ethanol and ether was added to the ethanolic solution. The precipitated crystals were collected by filtration to obtain sodium 2-(3'-methoxycinnamoylamino)phenylpropionate.

EXAMPLE 7

In a mixture of 50 ml of dioxane and 1 ml of pyridine were dissolved 1.18 g of 3-methoxy-4-propoxycinnamic acid and 0.91 g of methyl 4-aminophenylacetate. To this mixture was added 0.85 g of phosphorus oxychloride. The mixture was heated under reflux for 2 hours. The reaction mixture was then concentrated under reduced pressure and 50 ml of a 10% aqueous solution of sodium hydroxide were added to the residue. The mixture was warmed for one hour in a water bath and then weakly acidified with hydrochloric acid. The precipitated crystals were collected by filtration, recrystallized from ethanol-water and again recrystallized from benzene whereby 0.25 g of 4-(3'-methoxy-4'-propoxycinnamoylamino)phenylacetic acid was obtained. M.P. 183°–185° C. Other characteristics of this compound were as follows:

Elementary analysis as $C_{21}H_{23}O_5N$ Calcd. C, 68.28; H, 6.28; N, 3.79; Found C, 68.27; H, 6.22; N, 3.54.

IR-absorption spectra (KBr) $\nu$CO 1690 cm$^{-1}$, 1655 cm$^{-1}$;

NMR spectra (d$_6$-DMSO, 90 MHz); $\delta$ value 0.97 (t, 3H, J = 7.5Hz, methyl hydrogen in propoxy group); 1.5–1.96 (m, 2H, methylene hydrogen in propoxy group); 3.96 (t, 2H, J = 6.5Hz, methylene hydrogen in propoxy group); 3.52 (s, 2H, methylene hydrogen in benzyl group); 3.83 (s, 3H, methoxy hydrogen); 6.55–7.75 (m, 9H, olefinic hydrogen, aromatic ring hydrogen); 10.02 (s, 1H, carboxyl hydrogen).

184 Milligrams of 4-(3'-methoxy-4'-propoxycinnamoylamino)phenylacetic acid were dissolved in an alcohol and an equivalent amount of sodium hydroxide was added to the solution. The solution was warmed for 30 minutes. After cooling, ether was added to the solution and the precipitated crystals were collected by filtration to obtain sodium 4-(3'-methoxy-4'-propoxycinnamoylamino)phenylacetate.

EXAMPLE 8

In 100 ml of pyridine was dissolved 1.0 g of 4-aminophenoxyacetic acid. To this solution was added dropwise under cooling a solution of 1.4 g of 3,4-dimethoxycinnamoyl chloride in dioxane. The mixture was heated under reflux for 2 hours and thereafter, the reaction mixture was concentrated under reduced pressure. The residue was taken up in a small amount of ethanol and the ethanolic solution was poured into ice water. The aqueous mixture was made acidic by the addition of hydrochloric acid. The precipitated crystals were collected by filtration and recrystallized from alcohol-water whereby 1.7 g of 4-(3',4'-dimethoxycinnamoylamino)phenoxyacetic acid were obtained. M.P. 212°-216° C. Other characteristics of this compound were as follows:

Elementary analysis as $C_{19}H_{19}O_6N$ Calcd. C, 63.86; H, 5.36; N, 3.92; Found C, 63.57; H, 5.41; N, 3.67.

IR-absorption spectra (KBr) $\nu CO$ 1730 cm$^{-1}$, 1650 cm$^{-1}$;

NMR spectra (d$_6$-DMSO, 90 MHz) $\delta$ value 3.70–3.74 (s,s, 6H, methoxy hydrogen); 4.70 (s, 2H, methylene hydrogen); 6.90–8.20 (m, 9H, olefinic, aromatic ring hydrogen); 9.2 (s, 1H, carboxyl hydrogen).

357 Milligrams of 4-(3',4'-dimethoxycinnamoylamino)phenoxyacetic acid were dissolved in an alcohol and an equivalent amount of sodium hydroxide was added to the alcoholic solution. The solution was warmed for 30 minutes and then concentrated under reduced pressure. Ether was added to the residue to precipitate crystals which were then collected by filtration to obtain sodium 4-(3',4'-dimethoxycinnamoylamino)phenoxyacetate.

EXAMPLE 9

In a mixture of 30 ml of dioxane and 50 ml of pyridine were dissolved 1.8 g of 4-aminophenylacetic acid. To this solution was added dropwise under cooling and agitation a solution of 2.2 g of 4-acetoxycinnamoyl chloride in chloroform. The mixture was refluxed for 2 hours and thereafter, the reaction liquid was concentrated. The residue was warmed at 80° C for 30 minutes in 30 ml of a 10% aqueous solution of sodium hydroxide. The reaction liquid was then made weakly acidic by the addition of hydrochloric acid. The precipitated crystals were collected by filtration and recrystallized from alcohol-water whereby 1.6 g of 4-(4'-hydroxycinnamoylamino)phenylacetic acid were obtained. M.P. 243.5°–247° C. Other characteristics of this compound were as follows:

Elementary analysis as $C_{17}H_{15}O_4N$ Calcd. C, 68.67; H, 5.08; N, 4.71; Found C, 68.76; H, 5.12; N, 4.42.

IR-absorption spectra (KBr) $\nu CO$ 1690 cm$^{-1}$, 1655 cm$^{-1}$

NMR spectra (d$_6$-DMSO, 90 MHz) $\delta$ value 3.52 (s, 2H, methylene hydrogen); 6.50–7.70 (m, 10H, olefinic, aromatic ring hydrogen); 10.0 (s, 1H, carboxyl hydrogen).

289 Milligrams of 4-(4'-hydroxycinnamoylamino)phenylacetic acid were dissolved in an alcohol and an equivalent amount of sodium hydroxide was added to the solution. The solution was warmed for 30 minutes and then concentrated under reduced pressure. Ether was added to the residue and the precipitated crystals were collected by filtration to obtain sodium 4-(4'-hydroxycinnamoylamino)phenylacetate.

EXAMPLE 10

In a manner similar to that described in the foregoing examples, the compounds tabulated below were prepared from the corresponding starting materials.

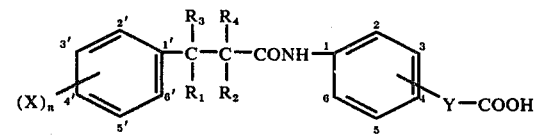

Table

| Compound No. | n | X | R$_1$ | R$_2$ | R$_3$ . R$_4$ | Y | Position of Y | M.P. | recrystallization solvent |
|---|---|---|---|---|---|---|---|---|---|
| 1 | 2 | 3'-OMe,4'-OMe | H | H | bond | —CH$_2$— | 2 | 178–182 | alcohol/water |
| 2 | 2 | 3'-OMe,4'-OMe | H | H | bond | —CH$_2$— | 3 | 172–176 | alcohol/water |
| 3 | 2 | 3'-OMe,4'-OMe | H | H | bond | —CH$_2$— | 4 | 184–190 | alcohol/water |
| 4 | 2 | 3'-OMe,4'-OMe | H | H | H. H | —CH$_2$— | 2 | 140–144 | benzene |
| 5 | 3 | 2'-OMe,4'-OMe, 5'-OMe | H | H | bond | —CH$_2$— | 4 | 192–194 | alcohol |
| 6 | 1 | 4'-Me | H | H | bond | —CH$_2$— | 2 | 194–197.5 | alcohol/water |
| 7 | 1 | 4'-iPr | H | H | bond | —CH$_2$— | 2 | 172–174 | alcohol/water |
| 8 | 1 | 4'-Cl | H | H | bond | —CH$_2$— | 2 | 208–213 | alcohol/water |
| 9 | 1 | 3'-OMe | H | H | bond | —CH$_2$— | 3 | 162–164 | alcohol/water |
| 10 | 2 | 3'-OMe,4'-iProxy | H | H | bond | —CH$_2$— | 2 | 194–197 | alcohol/water |
| 11 | 0 | — | H | H | bond | —CH$_2$— | 3 | 191–194 | alcohol/water |
| 12 | 2 | 3'-OMe,4'-OMe | H | H | bond | —CH(CH$_3$)— | 2 | 150–152 | benzene |
| 13 | 2 | 3'-OMe,4'-OMe | H | H | bond | —CH(CH$_3$)— | 3 | 169–171 | ethylacetate |
| 14 | 2 | 3'-OMe,4'-OMe | H | H | bond | —CH(CH$_3$)— | 4 | 169–173 | alcohol/water |
| 15 | 2 | 3'-OMe,4'-OMe | H | H | H . H | —CH(CH$_3$)— | 4 | 122–125 | alcohol/water |
| 16 | 1 | 4'-Me | H | H | bond | —CH(CH$_3$)— | 4 | 208–211 | alcohol/water |
| 17 | 1 | 2'-Me | H | H | bond | —(CH$_2$)$_3$— | 4 | 127–132 | alcohol/water |
| 18 | 1 | 3'-Cl or | H | H | bond | —(CH$_2$)$_3$— | 4 | 152–155.5 | alcohol/water |
| 19 | 2 | 3'-OMe,4'-OMe | H | H | bond | —O—CH$_2$— | 2 | 168–170 | alcohol/water |
| 20 | 2 | 3'-OMe,4'-OMe | H | H | bond | —O—CH$_2$ | 3 | 160–165 | alcohol/water |
| 21 | 2 | 3'-OMe,4'-OMe | H | H | H . H | —O—CH$_2$— | 2 | 117–120 | alcohol/water |
| 22 | 2 | 3'-OMe,4'-OMe | CH$_3$ | H | bond | —O—CH$_2$— | 2 | 165–167 | alcohol/water |
| 23 | 1 | 4'-Me | H | H | H . H | —O—CH$_2$— | 4 | 188–189 | alcohol/water |
| 24 | 1 | 4'-Cl | CH$_3$ | H | bond | —O—CH$_2$— | 4 | 215–217 | alcohol/water |

Table-continued

| Compound No. | n | X | $R_1$ | $R_2$ | $R_3 \cdot R_4$ | Y | Position of Y | M.P. | recrystallization solvent |
|---|---|---|---|---|---|---|---|---|---|
| 25 | 1 | 4'-Me | $CH_3$ | H | bond | $-O-CH_2-$ | 4 | 177–179 | alcohol/water |
| 26 | 2 | 3'-OMe,4'-Proxy | H | H | bond | $-O-CH_2-$ | 2 | 96–99 | alcohol/water |
| 27 | 0 | — | H | $CH_3$ | bond | $-O-CH_2-$ | 4 | 185–190 | alcohol/water |
| 28 | 2 | 3'-OMe,4'-OMe | $CH_3$ | H | bond | $-CH_2-$ | 2 | 161–164 | ethylacetate |
| 29 | 1 | 4'-Me | H | H | bond | $-O-CH_2-$ | 4 | 213–219 | alcohol/water |
| 30 | 1 | 4'-iPr | H | H | bond | $-O-CH_2-$ | 2 | 148–152 | alcohol/water |
| 31 | 1 | 4'-Cl | H | H | bond | $-O-CH_2-$ | 4 | 220–223 | alcohol/water |
| 32 | 1 | 4'-Cl | H | H | bond | $-O-CH_2-$ | 2 | 182–187 | alcohol/water |
| 33 | 2 | 3'-OMe,4'-OMe | $CH_3$ | H | bond | $-O-CH_2-$ | 4 | 165–168 | alcohol/water |
| 34 | 1 | 4'-Cl | H | H | bond | $-O-CH(CH_3)-$ | 2 | 160–164 | alcohol/water |
| 35 | 2 | 3'-OMe,4'-OMe | H | H | bond | $-O-CH(CH_3)-$ | 3 | 198–203 | alcohol/water |
| 36 | 2 | 3'-OMe 4'-OCH=CHCH_3 | H | H | bond | $-O-CH_2-$ | 4 | 191–193 | chloroform |
| 37 | 1 | 4'-Ph | H | H | bond | $-O-CH_2-$ | 4 | 224–226 | alcohol/water |
| 38 | 2 | 3',4'-trimethylene | H | H | bond | $-O-CH_2-$ | 4 | 190–195 | alcohol/water |
| 39 | 2 | 3'-OMe,4'-OMe | H | H | bond | $-O-(CH_2)_3-$ | 4 | 185–190 | alcohol/water |
| 40 | 1 | 4'-Me | H | H | bond | $-O-(CH_2)_5-$ | 4 | 173–176 | alcohol/water |
| 41 | 2 | 2'-OMe,4'-OMe | H | H | bond | $-CH_2-$ | 4 | 218–221 | alcohol/water |
| 42 | 1 | 4'-Me | H | H | bond | $-CH_2-$ | 2 | 194–197.5 | alcohol/water |
| 43 | 1 | 2'-F | H | H | bond | $-CH_2-$ | 3 | 205–213 | alcohol/water |
| 44 | 2 | 3'-OMe,4'-OH | H | H | bond | $-CH_2-$ | 4 | 165–168 | alcohol/water |
| 45 | 3 | 2'-OMe,4'-OMe 5'-OMe | H | H | bond | $-CH(CH_3)-$ | 4 | 242–244 | alcohol |
| 46 | 2 | 3'-OMe 4'-OCH=CHCH_3 | H | H | bond | $-CH_2-$ | 4 | 168–170 | chloroform |
| 47 | 1 | 4'-OMe | H | $CH_3$ | bond | $-CH_2-$ | 4 | 177–179 | alcohol/water |
| 48 | 1 | 4'-Me | H | $CH_3$ | bond | $-CH_2-$ | 4 | 178–181 | alcohol/water |
| 49 | 2 | 3',4'-methylenedioxy | H | H | bond | $-(CH_2)_2-$ | 2 | 183–186 | alcohol/water |
| 50 | 1 | 3'-Cl | H | H | bond | $-(CH_2)_2-$ | 3 | 130–131 | alcohol/water |
| 51 | 1 | 4'-OMe | H | $CH_3$ | bond | $-(CH_2)_2-$ | 3 | 161–162 | alcohol/water |
| 52 | 1 | 4'-Cl | H | $CH_3$ | bond | $-CH(CH_3)-$ | 4 | 173–175 | alcohol/water |
| 53 | 1 | 4'-Br | H | $CH_3$ | bond | $-(CH_2)_3-$ | 4 | 140–142 | alcohol/water |
| 54 | 2 | 3'-OMe,4'-OMe | H | $CH_3$ | bond | $-CH(CH_3)CH_2-$ | 4 | 132–133 | alcohol/water |
| 55 | 1 | 4'-Cl | H | H | bond | $-C(CH_3)_2-$ | 4 | 272–273 | alcohol/water |
| 56 | 3 | 2'-OMe,4'-OMe, 5'-OMe | H | $CH_3$ | bond | $-C(CH_3)_2-$ | 4 | 175–176 | alcohol/water |
| 57 | 1 | 4'-OMe | H | H | bond | $-(CH_2)_2-$ | 2 | 223–224.5 | alcohol/water |
| 58 | 3 | 2'-OMe,4'-OMe, 5'-OMe | H | H | bond | $-(CH_2)_5-$ | 4 | 138–140 | alcohol/water |
| 59 | 1 | 4'-Cl | H | $CH_3$ | bond | $-CH_2-$ | 3 | 154–155 | alcohol/water |
| 60 | 1 | 4'OCH=C(CH_3)_2 | H | H | bond | $-O-CH_2-$ | 4 | 197–199 | alcohol/water |
| 61 | 1 | 4'-OCH=CHCH_3 | H | H | bond | $-O-CH_2-$ | 4 | 213–216 | alcohol/water |
| 62 | 2 | 3'-OCH=CH(CH_3) 4'-OMe | H | H | bond | $-O-CH_2-$ | 4 | 197–201 | alcohol/water |
| 63 | 2 | 3'-CH=C(CH_3)_2 4'-OMe | H | H | bond | $-O-CH_2-$ | 4 | 157–160 | alcohol/water |
| 64 | 2 | 4'-OCOCH_3,3'-OMe | H | H | bond | $-O-CH_2-$ | 3 | 95–97 | alcohol/water |
| 65 | 2 | 4'-OH,3'-OMe | H | H | bond | $-O-CH_2-$ | 3 | 103–106 | alcohol/water |
| 66 | 1 | 4'-OMe | $CH_3$ | H | bond | $-CH(CH_3)-$ | 3 | 152–155 | alcohol/water |
| 67 | 1 | 4'-Me | H | H | bond | $-O-(CH_2)_5-$ | 4 | 173–176 | alcohol/water |
| 68 | 2 | 3'-OMe,4'-OMe | H | H | bond | $-O-(CH_2)_3-$ | 4 | 185–190 | alcohol/water |

EXAMPLE 9

Homologous passive cutaneous anaphylaxis (PCA) in rats

Wistar male rats weighing from 120 to 150 g were used in the present experiment. Reaginic antibody was obtained from rats immunized with 2,4-dinitrophenyl-coupled ascaris extract (DNP-As) mixed with *Bordetella pertussis*. Normal rats were sensitized passively with an intradermal injection of the diluted antiserum. After 48 hours of the sensitization, the mixture of antigen (DNP-As) and Evans blue was injected intravenously. The animals were sacrificed by a blow on the head 30 minutes after challenging with antigen. The area blued as a result of PCA was excised and the amount of dye leaked was measured photometrically after the extraction of same with acetone containing sodium carbonate.

The test compounds were suspended in 0.5% aqueous solution of sodium carboxymethylcellulose (CMC) and administered 200 mg/kg p.o. 2 hours prior to the injection of a mixture of antigen and Evans blue. Chlorphenesin[1] used as a positive control is generally well-known as an inhibitor of mast cell disruption resulted in the allergic reaction. The efficacy of the test compounds to inhibit the PCA was compared with the value (%) calculated using the following formula:

$$\text{Inhibition (\%)} = \frac{A - B}{A} \times 100$$

A : Amount of dye leaked in the control group
B : Amount of dye leaked in the group treated with test compound It seems likely that PCA in rats is useful to determine whether a test compound inhibits the allergic response or not.

The results of the tests are shown below.

| COMPOUND | INHIBITION (%) |
| --- | --- |
| control | 0 |
| chlorphenesin | 39.7 |
| N-cinnamoyl-anthranilic acid | 18.1 |
| 3-(cinnamoylamino)benzoic acid | 10.8 |
| 4-(cinnamoylamino)benzoic acid | 7.5 |
| 2-(3',4'-dimethoxycinnamoylamino)phenylacetic acid | 63.9 |
| 2-(3',4'-dimethoxy-β-methylcinnamoylamino)phenylacetic acid | 37.3 |
| β-[2-(3',4'-dimethoxycinnamoylamino)]phenylpropionic acid | 27.0 |
| β-[3-(3',4'-dimethoxycinnamoylamino)]phenylpropionic acid | 47.2 |
| 2-(3',4'-dimethoxycinnamoylamino)phenoxyacetic acid | 42.6 |
| β-[4-(4'-methylcinnamoylamino)]phenoxyacetic acid | 75.9 |
| 3-(cinnamoylamino)phenylacetic acid | 39.8 |
| 4-(4'-methoxy-β-cinnamoylamino)phenylacetic acid | 85.3 |
| 4-(4'-hydroxycinnamoylamino)phenylacetic acid | 34.3 |
| 2-(3'-methoxy,4'-propoxycinnamoylamino)phenoxyacetic acid | 32.1 |
| 2-(3',4'-dimethoxyhydrocinnamoylamino)phenoxyacetic acid | 25.9 |
| 2-(4'-chlorocinnamoylamino)phenylacetic acid | 53.3 |

What is claimed is:

1. Compounds of the general formula:

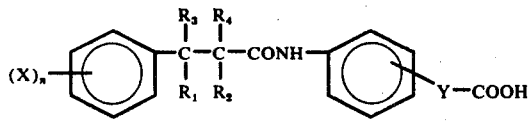

wherein $R_1$ and $R_2$ each represent a hydrogen atom or an alkyl group with 1-4 carbon atoms; $R_3$ and $R_4$ each represent a hydrogen atom or may be combined together to form another chemical bond; X represents a hydroxyl group, a halogen atom, a straight or branched chain saturated or unsaturated alkyl group with 1-4 carbon atoms, a straight or branched chain saturated or unsaturated alkoxy group with 1-4 carbon atoms, an acyloxy group with 1-4 carbon atoms, or a cycloalkyl group with up to 6 carbon atoms; n is zero or an integer of 1-3 with the proviso that when n is 2 or 3, X's may be same or different and that when two X's are commonly said alkyl or alkoxy group, both X's may be combined together to form a ring; and Y represents a straight or branched chain alkylene group or a straight or branched chain oxyalkylene group connected to the benzene ring through the oxygen atom, as well as physiologically acceptable salts thereof.

2. Compounds according to claim 1 wherein $R_3$ and $R_4$ are combined together to form another chemical bond so that said compounds can be represented by the general formula:

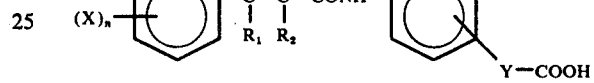

wherein X, n, $R_1$, $R_2$ and Y have the same meanings as given above.

3. Compounds according to claim 1 wherein $R_3$ and $R_4$ each represent a hydrogen atom.

4. Compounds according to claim 3 wherein at least one of $R_1$ and $R_2$ stands for an alkyl group with 1-4 carbon atoms and the other for a hydrogen atom.

5. Compounds according to claim 2 wherein at least one of $R_1$ and $R_2$ stands for an alkyl group with 1-4 carbon atoms and the other for a hydrogen atom.

6. A compound as in claim 2 wherein X is methoxy, n is 2, $R_1$ is methyl, $R_2$ is hydrogen, and Y is methylene.

7. A Pharmaceutical composition which comprises a pharmaceutically effective amount of compound as claimed in claim 1 and an inert, non-toxic pharmaceutically acceptable carrier.

* * * * *